United States Patent
Sherman

(12) 
(10) Patent No.: US 6,197,335 B1
(45) Date of Patent: Mar. 6, 2001

(54) SOLID PHARMACEUTICAL COMPOSITIONS COMPRISING A CYCLOSPORIN AND AN ANIONIC SURFACTANT

(75) Inventor: Bernard Charles Sherman, 50 Old Colony Road, Willowdale (CA), M2L 2KI

(73) Assignee: Bernard Charles Sherman, Willowdale (CA)

( * ) Notice: Subject to any disclaimer, the term of this patent is extended or adjusted under 35 U.S.C. 154(b) by 0 days.

(21) Appl. No.: 09/308,272

(22) PCT Filed: Sep. 16, 1998

(86) PCT No.: PCT/CA98/00880

§ 371 Date: May 17, 1999

§ 102(e) Date: May 17, 1999

(87) PCT Pub. No.: WO99/13900

PCT Pub. Date: Mar. 25, 1999

(30) Foreign Application Priority Data

Sep. 16, 1997 (NZ) ........................................... 328751

(51) Int. Cl.⁷ ............... A61K 9/20; A61K 9/48; A61K 9/64; A61K 38/00
(52) U.S. Cl. ............... 424/464; 424/451; 424/456; 424/465; 514/9
(58) Field of Search ................................. 424/451, 456, 424/464, 465; 514/9

(56) References Cited

U.S. PATENT DOCUMENTS

| | | |
|---|---|---|
| 4,388,330 | 6/1983 | Cavanak . |
| 5,342,625 | 8/1994 | Hauner et al. . |
| 5,674,521 * | 10/1997 | Gehrke et al. ................... 424/423 |
| 5,741,524 * | 4/1998 | Stainforth et al. ............... 424/489 |
| 5,756,450 * | 5/1998 | Hahn et al. ........................ 514/9 |
| 5,891,845 * | 4/1999 | Myers ............................... 514/11 |

FOREIGN PATENT DOCUMENTS

| | | |
|---|---|---|
| 0 294 239 | 12/1988 | (EP) . |
| 2536876 | 2/1989 | (JP) . |

OTHER PUBLICATIONS

Abdallaha and Mayersohn, "The Preparation and Evaluation of a Tablet Dosage Form of Cyclosporine in Dogs", Pharmaceutical Research 8(4):518–522 (1991).

* cited by examiner

*Primary Examiner*—Thurman K. Page
*Assistant Examiner*—S. Tran
(74) *Attorney, Agent, or Firm*—Ivor M. Hughes; Neil H. Hughes; Marcelo K. Sarkis

(57) ABSTRACT

A solid pharmaceutical composition for oral administration comprising a cyclosporin and an anionic surfactant, preferably sodium lauryl sulfate, wherein the amount of anionic surfactant is at least about forty percent of the minimum amount needed to dissolve the cyclosporin in water.

22 Claims, No Drawings

SOLID PHARMACEUTICAL COMPOSITIONS COMPRISING A CYCLOSPORIN AND AN ANIONIC SURFACTANT

TECHNICAL FIELD

Solid pharmaceutical compositions for oral administration of cyclosporins.

BACKGROUND ART

The term "cyclosporin" as used herein refers to any member of a class of nonpolar polypeptides, as defined in the Merck Index, Twelfth Edition. One such cyclosporin is cyclosporin A, also known as "cyclosporine" and hereinafter referred to as "cyclosporine", known to be therapeutically active as an immunosuppressant.

Cyclosporins are hydrophobic and have low solubility in aqueous media. This makes it difficult to design pharmaceutical compositions (i.e. dosage forms) comprising cyclosporins which exhibit satisfactory absorption into systemic circulation after oral administration.

The cyclosporin can be dissolved in an organic solvent (e.g. ethanol or propylene glycol), but, if the solvent is water-miscible, when the composition is mixed with gastrointestinal fluid or other aqueous medium, the cyclosporin will precipitate.

Methods of overcoming this problem are known in the prior art. The most common approach is to dissolve the cyclosporin in a solvent system that comprises at least one lipophilic (hydrophobic) solvent and a surfactant, so that the composition disperses into an emulsion when mixed into gastrointestinal fluid or other aqueous medium.

Such compositions are called "emulsion preconcentrates".

U.S. Pat. No. 4,388,307 discloses such compositions. A commercial product that has been sold under the trademark Sandimmune (registered trademark) is made according to U.S. Pat. No. 4,388,307, and, more specifically, comprises cyclosporine dissolved in a solvent system comprising ethanol as hydrophilic solvent, a vegetable oil as lipophilic solvent, and a surfactant. The ethanol is required to dissolve the cyclosporine in the composition, as the vegetable oil has inadequate capacity to dissolve cyclosporins.

Sandimmune (registered trademark) is sold in the form of both an oral liquid, which is an emulsion preconcentrate intended to be diluted into an aqueous drink before ingestion, and a soft gelatin capsule containing the emulsion preconcentrate.

U.S. Pat. No. 5,342,625 discloses compositions that are superior in certain respects to the compositions taught in U.S. Pat. No. 4,388,307. The compositions of U.S. Pat. No. 5,342,625 again comprise, cyclosporine, a hydrophilic solvent, a lipophilic (i.e. hydrophobic) solvent and a surfactant. The hydrophilic solvent is either propylene glycol or an alkyl or tetrahydrofurfuryl di- or partial-ether of a low molecular weight mono- or poly-oxy-alkanediol.

Compositions according to U.S. Pat. No. 5,342,625, when added to water, disperse into emulsions with droplet size of less than 2000 Å which is smaller than those obtained with prior art compositions, thus leading to improved absorption.

Emulsions with droplet size of less than 2000 Å are defined as "microemulsions". Compositions that, upon addition to water, disperse into microemulsions are called "microemulsion preconcentrates".

A composition made according to the disclosure of U.S. Pat. No. 5,342,625 is now marketed under the trademark Neoral (registered trademark). As is the case with Sandimmune (registered trademark), Neoral (registered trademark) is available as both an oral liquid and soft gelatin capsules.

For both the soft gelatin capsules and the oral liquid, Neoral (registered trademark) microemulsion preconcentrate comprises cyclosporine dissolved in ethanol and propylene glycol as hydrophilic solvents, corn oil glycerides as lipophilic solvent, and polyoxyl 40 hydrogenated castor oil as surfactant. It also contains dl-alpha-tocopherol at a level of about one percent by weight as antioxidant.

For both Sandimmune (registered trademark) and Neoral (registered trademark), the capsule formulations have certain undesirable features.
Specifically:

1. They both contain ethanol, which is volatile. This means that the capsules must be individually packaged in metal pouches to avoid evaporation of the ethanol.

2. The capsules are relatively large and difficult to swallow. This is because the formulations must contain substantial quantities of the hydrophilic and lipophilic solvents, which are needed to keep the cyclosporine and surfactant in solution. The total weight of contents of each capsule is about ten times the weight of the cyclosporine contained therein.

The prior art discloses some attempts to overcome these problems by use of formulations that contain the cyclosporin and surfactant, but no solvent.

Such compositions are solid in form and can be used to make tablets or as a fill for two-piece hard gelatin capsules.

Japanese No. 2536876 of Takada et al discloses powdery preparations comprising a cyclosporin dispersed in a solid, non-surfactant carrier together with a surfactant. All of the examples in this patent use as the surfactant polyoxyethylene hydrogenated castor oil, which is non-ionic. In the examples, the total weight of the compositions is from 5 to 151 times the weight of the cyclosporin, and it appears unlikely that any of the disclosed compositions, particularly those with smaller amounts of the inactive ingredients, would give absorption in humans equivalent to that of Sandimmune (registered trademark) or Neoral (registered trademark).

European Application No. 88305138.5 (publication No. 0294239) of Kurihara and Murano discloses solid compositions comprising a cyclosporin in admixture with an amount of alpha-cyclodextrin or a functional derivative thereof sufficient to solubilize the cyclosporin in water. However, the amount of alpha-cyclodextrin required is generally many times the amount of cyclosporin by weight, so that this approach appears incapable of providing dosage forms smaller than Sandimmune (registered trademark) or Neoral (registered trademark) capsules. Additionally, there is no indication that any of the disclosed compositions will, upon oral administration, give absorption equivalent to that of Sandimmune (registered trademark) or Neoral (registered trademark).

In Pharmaceutical Research, Vol. 8, No. 4, 1991, pp 518–522, Abdallah and Mayersohn disclose a tablet containing cyclosporine 100 mg, mannitol 250 mg, microcrystalline cellulose 200 mg, stearic acid 20 mg, and sodium dodecyl sulfate 10 mg. It is stated that the tablets gave absorption comparable to that of Sandimmune (registered trademark) in a comparative bioavailability study in dogs.

However, the relatively large amount of inactive ingredients used precludes tablets or capsules significantly smaller than Sandimmune (registered trademark) or Neoral (registered trademark), and there is no evidence given that such a formulation would give absorption equivalent to that of Sandimmune or Neoral in humans.

In view of the problems with prior art formulations, it is the object of the present invention to enable pharmaceutical compositions containing a cyclosporin (and in particular cyclosporine) with the following properties:

1. They are solid at room temperature and free of volatile solvents.
2. Upon oral administration, they enable absorption comparable to that of Sandimmune (registered trademark) or Neoral (registered trademark).
3. They enable capsules or tablets of smaller size than Sandimmune (registered trademark) and Neoral (registered trademark). That is to say, they enable compositions wherein the content of the cyclosporin by weight exceeds ten percent and preferably twenty percent of the weight of the composition.

BRIEF SUMMARY OF THE INVENTION

It has surprisingly been found that the objects of the invention can be achieved by a pharmaceutical composition comprising a cyclosporin in admixture with an anionic surfactant, wherein the amount of anionic surfactant is at least about forty percent of the minimum quantity that would be needed to dissolve the cyclosporin in water, using a quantity of water small enough that the concentration of the anionic surfactant in the water would exceed the critical micelle concentration.

DETAILED DESCRIPTION OF THE INVENTION

Anionic surfactants usable within the scope of the invention will include any anionic surfactant that is solid at normal room temperature (20° C. to 25° C.) and of sufficiently low toxicity that it is acceptable for oral administration in a pharmaceutical product.

The most commonly used anionic surfactants are those containing carboxylate, sulfonate, and sulfate ions.

Preferred anionic surfactants are sodium-alkyl sulfates and sulfonates, and sodium alkyl aryl sulfonates.

Most preferred is sodium lauryl sulfate (also known as sodium dodecyl sulfate), which is widely used as an emulsifier and solubilizer in pharmaceutical products.

The ability of anionic surfactants to solubilize cyclosporins in water substantially increases when the concentration of the surfactant in water substantially exceeds the critical micelle concentration.

Using sodium lauryl sulfate, for example, the critical micelle concentration is about 0.1% by weight.

At concentrations of sodium lauryl sulfate in water under 0.1%, the amount of cyclosporine that will dissolve is less than 50% by weight of the amount of sodium lauryl sulfate dissolved, but at concentrations of sodium lauryl sulfate in water of 1% or more, the amount of cyclosporine that will dissolve is about equal by weight to the amount of sodium lauryl sulfate dissolved.

As aforesaid, compositions with the scope of the invention are compositions wherein the quantity of anionic surfactant is at least about forty percent of the minimum quantity that would be needed to dissolve the cyclosporin in water, using a quantity of water small enough that the concentration of the anionic surfactant in the water would exceed the critical micelle concentration.

Using cyclosporine and sodium lauryl sulfate, for example, it follows that compositions within the scope of the invention would be compositions wherein the amount of sodium lauryl sulfate is at least about forty percent by weight of the amount of cyclosporine. The amount of sodium lauryl sulfate will preferably be at least about eighty percent by weight of the amount of cyclosporine.

Because of toxicity concerns, the amount of anionic surfactant should not exceed that which is needed to enable satisfactory absorption of the drug upon oral administration.

The amount of anionic surfactant will preferably not exceed about four times the minimum quantity that would be needed to dissolve the cyclosporin in water, again using a quantity of water small enough that the concentration of the surfactant in the water would exceed the critical micelle concentration.

It follows, for example, that in the case of compositions comprising cyclosporine and sodium lauryl sulfate, the amount of sodium lauryl sulfate by weight preferably will not exceed four times the amount of cyclosporine. Most preferably it will not exceed three times the amount of cyclosporine.

To enable small capsules or tablets, the cyclosporin will preferably comprise at least ten percent, and most preferably at least twenty percent, of the composition by weight.

Compositions within the scope of the invention can be made by mixing the cyclosporin and anionic surfactant, optionally with other ingredients, in dry form and then further processing the mixed powder into tablets or filling the mixed powder into empty two-piece hard gelatin capsules.

However, the effectiveness of the surfactant is increased and the amount needed is to achieve adequate absorption of the drug is thus decreased, if, in the process of manufacture of the composition, the cyclosporin and the anionic surfactant are dissolved together (optionally along with other ingredients) in a solvent or a solvent system, and the solvent or solvents are then evaporated to give a dry co-precipitate of the cyclosporin and anionic surfactant.

The evaporation of the solvent or solvents will preferably be done by spray-drying or freeze-drying, most preferably by spray-drying.

In cases in which the amount of anionic surfactant being used is sufficient to fully dissolve the cyclosporin in water, water can be used as the sole solvent. If the amount of surfactant is less than needed to fully dissolve the cyclosporin in water, then the cyclosporin and surfactant can be dissolved in a solvent system comprising a mixture of water and an organic solvent, preferably a volatile alcohol such as methanol.

The invention will be further illustrated by the following examples, which are intended to be illustrative but not limiting of the scope of the invention.

EXAMPLE 1

50.0 g of cyclosporine, 55.0 g of sodium lauryl sulfate, and 40.0 g lactose monohydrate were mixed together in dry form.

The mixed powder was filled into size 2 capsules at a net fill weight of 290 mg per capsule. Each capsule thus contained 100 mg of cyclosporine, 110 mg of sodium lauryl sulfate and 80 mg of lactose monohydrate.

EXAMPLE 2

200.0 g of cyclosporine, 220.0 g of sodium lauryl sulfate, and 160.0 g of mannitol were dissolved together in 2000.0 g of water. The solution was then spray-dried. The spray-dried powder was then compacted, and then ground into granules. The granules were then filled into size 2 capsules at a net fill weight of 290 mg per capsule. Each capsule thus contained 100 mg of cyclosporine, 110 mg of sodium lauryl sulfate, and 80 mg of mannitol.

EXAMPLE 3

200.0 g of cyclosporine, 440.0 g of sodium lauryl sulfate and 160.0 g of mannitol were dissolved together in 2000.0 g of water. The solution was then spray-dried.

The spray-dried powder was then compacted, and then ground into granules. The granules were then filled into size 1 capsules at a net fill weight of 400 mg per capsule. Each capsule thus contained 100 mg of cyclosporine, 220 mg of sodium lauryl sulfate, and 80 mg of mannitol.

EXAMPLE 4

500.0 g of cyclosporine and 1200.0 g of sodium lauryl sulfate were dissolved together in 5500 g of water. The solution was then spray-dried. The spray-dried powder was then compacted, and then ground into granules. The granules were then filled into size 1 capsules at a net fill weight of 340 mg per capsule. Each capsule then contained 100 mg of cyclosporine and 240 mg of sodium lauryl sulfate.

EXAMPLE 5

500.0 g of cyclosporine and 400.0 g of sodium lauryl sulfates were dissolved together in a mixture of water and methanol. The solution was then spray-dried. The spray-dried powder was then compacted, and then ground into granules. The granules were then filled into size 3 capsules at a net fill weight of 180 mg per capsule. Each capsule thus contained 100 mg of cyclosporine and 80 mg of sodium lauryl sulfate.

Comparative Bioavailability Studies

A 3-way comparative bioavailability study was done in 6 human volunteers to compare the absorption of the capsules of example 1 and the capsules of example 2 to Sandimmune (registered trademark) capsules 100 mg. Over a period of 72 hours from ingestion, the mean extent of the absorption was found to be 96% of that of Sandimmune (registered trademark) for the capsules of example 1 and 121% of that of Sandimmune (registered trademark) for the capsules of example 2.

A 3-way comparative bioavailability study was done in 6 human volunteers to compare the absorption of the capsules of example 2 and the capsules of example 3 to Neoral (registered trademark) capsules 100 mg. Over a period of 72 hours from ingestion, the mean extent of absorption was found to be 73% of that of Neoral (registered trademark) for the capsules of example 2 and 92% of that of Neoral (registered trademark) for the capsules of example 3.

What is claimed is:

1. A solid pharmaceutical composition for oral administration comprising a cyclosporin and a surfactant, wherein said surfactant consists essentially of an anionic surfactant and wherein the amount of said anionic surfactant is at least about forty percent of the minimum amount that would be needed to dissolve the cyclosporin in water using a quantity of water small enough that the concentration of the anionic surfactant in the water would exceed the critical micelle concentration and wherein the amount of anionic surfactant by weight is from about 40% to about 400% of the amount of the cyclosporin.

2. A composition as in claim 1 wherein the amount of said anionic surfactant is not more than about four times the minimum amount that would be needed to dissolve the cyclosporin in water using a quantity of water small enough that the concentration of the anionic surfactant in water would exceed the critical micelle concentration.

3. A composition as in claim 1 wherein the anionic surfactant is selected from the group consisting sodium alkyl sulfates, sodium alkyl sulfonates and sodium alkyl aryl sulfonates.

4. A composition as in claim 1 wherein the anionic surfactant is sodium lauryl sulfate.

5. A composition as in claim 1 wherein the amount of sodium lauryl sulfate by weight is from about 80% to about 300% of the amount of the cyclosporin.

6. A composition as in claim 1, wherein the cyclosporin comprises more than ten percent of the composition by weight.

7. A composition as in claim 1, wherein the cyclosporin comprises more than twenty percent of the composition by weight.

8. A composition as in claim 1, wherein the cyclosporin is cyclosporine.

9. A composition as in claim 1 contained within a 2-piece hard gelatin capsule.

10. A composition as in claim 1 in the form of a tablet.

11. A process of making a composition as in claim 1 comprising the steps of dissolving the cyclosporin and anionic surfactant in a solvent or a combination of solvents and then evaporating the solvent or solvents.

12. A process as in claim 11 wherein water is used as solvent.

13. A process as in claim 11 wherein the evaporation is done by spray-drying.

14. A solid pharmaceutical composition comprising a cyclosporin and a surfactant wherein said surfactant consists essentially of sodium lauryl sulfate, wherein the amount of sodium lauryl sulfate by weight is from about 80% to about 400% of the cyclosporin.

15. A process of making a composition in claim 14 comprising the steps of dissolving the cyclosporin and anionic surfactant in a solvent or a combination of solvents and then evaporating the solvent or solvents.

16. The process as in claim 15 wherein water is used as solvent.

17. The process as in claim 15 or 16 wherein the evaporation is done by spray-drying.

18. The composition as in claim 14, wherein the cyclosporin comprises more than ten percent of the composition by weight.

19. The composition as in claim 14, wherein the cyclosporin comprises more than twenty percent of the composition by weight.

20. A composition as in claim 14, wherein the cyclosporin is cyclosporin.

21. A composition as in claim 14, contained within a 2-piece hard gelatin capsule.

22. A composition as in claim 14 in the form of a tablet.

* * * * *